(12) United States Patent
Rendu et al.

(10) Patent No.: US 8,802,363 B2
(45) Date of Patent: Aug. 12, 2014

(54) ZEODRATION METHOD FOR THE PRESERVATION OF BLOOD PLATELETS

(75) Inventors: Francine Rendu, Paris Cedex 13 (FR); Thibault Donnet, Paris Cedex 13 (FR); Christian Gachet, Strasbourg Cedex (FR); Jean-Pierre Cazenave, Strasbourg Cedex (FR)

(73) Assignees: Inserm (Institut National de la Sante et de la Recherche Medicale), Paris (FR); Universite de Strasbourg, Strasbourg (FR); Etablissement Francais du Sang, La Plaine Saint Denis Cedex (FR)

( * ) Notice: Subject to any disclaimer, the term of this patent is extended or adjusted under 35 U.S.C. 154(b) by 0 days.

(21) Appl. No.: 13/637,459

(22) PCT Filed: Nov. 26, 2010

(86) PCT No.: PCT/EP2010/068320
§ 371 (c)(1),
(2), (4) Date: Dec. 10, 2012

(87) PCT Pub. No.: WO2011/124280
PCT Pub. Date: Oct. 13, 2011

(65) Prior Publication Data
US 2013/0078608 A1    Mar. 28, 2013

(30) Foreign Application Priority Data
Apr. 8, 2010 (EP) .................................. 10305358

(51) Int. Cl.
G01N 33/48 (2006.01)
G01N 33/49 (2006.01)
A01N 1/02 (2006.01)

(52) U.S. Cl.
CPC ............ *A01N 1/0289* (2013.01); *A01N 1/0284* (2013.01); *G01N 33/49* (2013.01)
USPC ...................................... 435/2; 436/8; 436/16

(58) Field of Classification Search
None
See application file for complete search history.

(56) References Cited

U.S. PATENT DOCUMENTS

| 6,723,497 B2 * | 4/2004 | Wolkers et al. ..................... 435/2 |
| 2005/0009000 A1 * | 1/2005 | Wilhelm et al. ............... 435/1.1 |
| 2007/0243178 A1 * | 10/2007 | Ho et al. .................... 424/93.72 |
| 2008/0215364 A1 * | 9/2008 | Brevnova et al. ................ 705/2 |

FOREIGN PATENT DOCUMENTS

| FR | 2836482 A1 * | 2/2002 | ............... C12N 5/02 |
| WO | 03/013239 | 2/2003 | |
| WO | 2007/027178 | 3/2007 | |

OTHER PUBLICATIONS

Donnet, T. Development of a new method of conservation of blood platelets: application of zeodration technology. Sep. 2005. Abstract from Centre de Recherche sur les Biotechnologies Marines. BulletInfo No. 5, p. 11: English translation attached, $2^{nd}$ page.*
International Search Report in PCT/EP2010/068320 dated May 11, 2011.

* cited by examiner

*Primary Examiner* — John S Brusca
*Assistant Examiner* — Sharon M Papciak
(74) *Attorney, Agent, or Firm* — McAndrews, Held & Malloy Ltd.

(57) ABSTRACT

The present invention relates to a new method for the preservation of blood platelets. In particular, the present invention provides a method which includes submitting the platelets to zeodration carried out at temperatures between 18° C. and 24° C. The dried platelets thus obtained can be preserved at room temperature for long period of time. The invention also provides kits and compositions for using the preserved platelets.

15 Claims, 9 Drawing Sheets

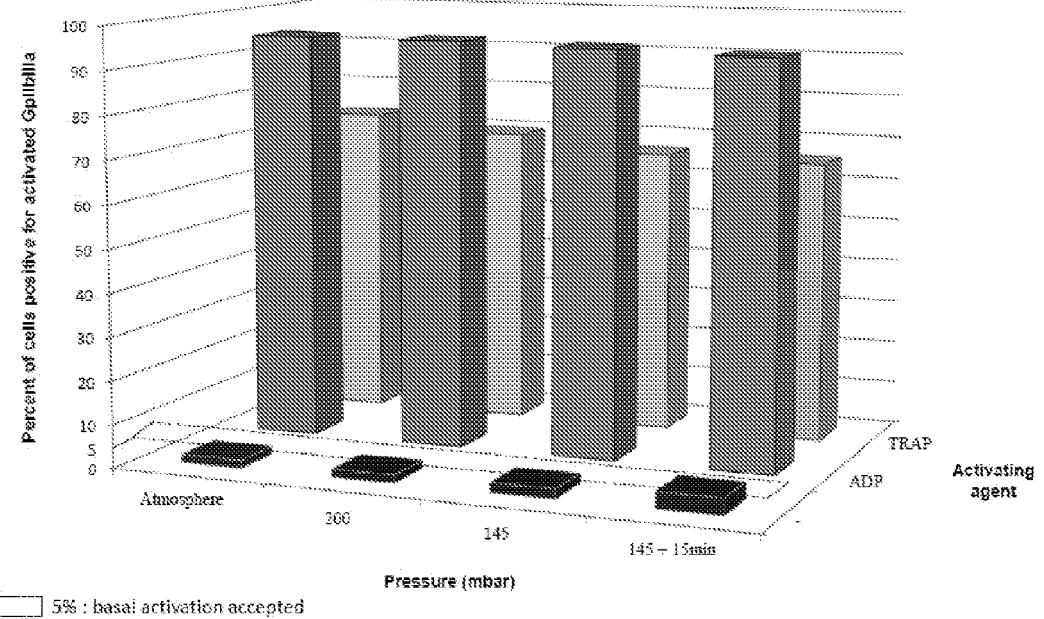
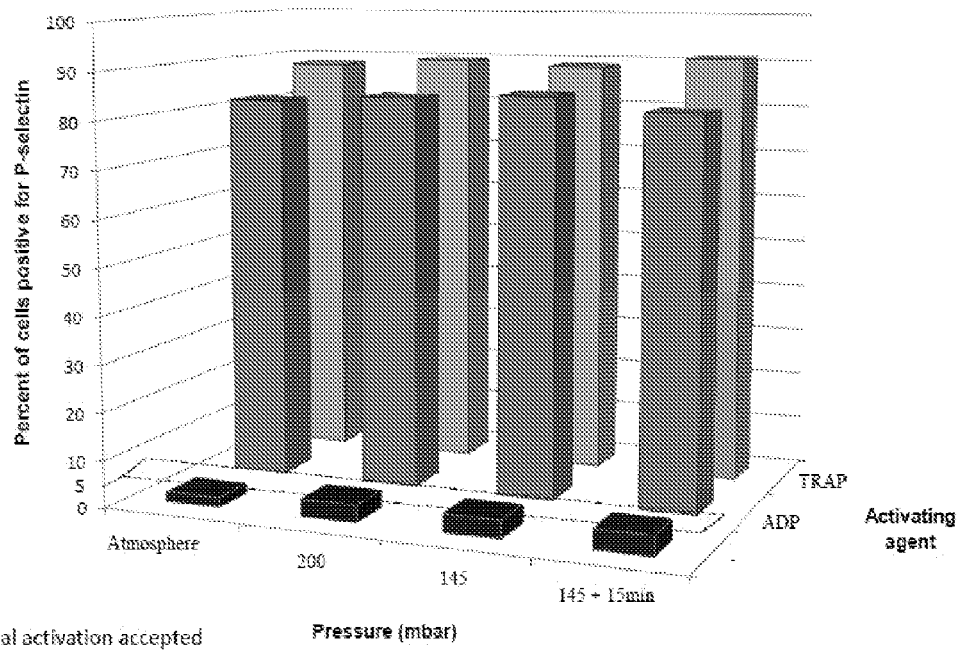
Figure 2(A)-(B)

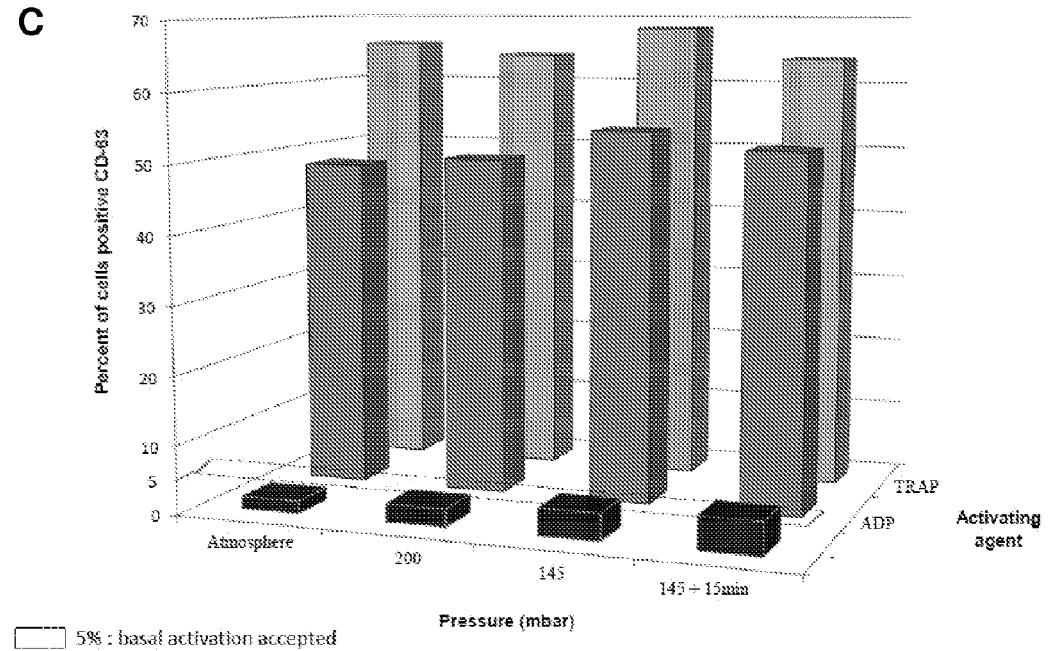
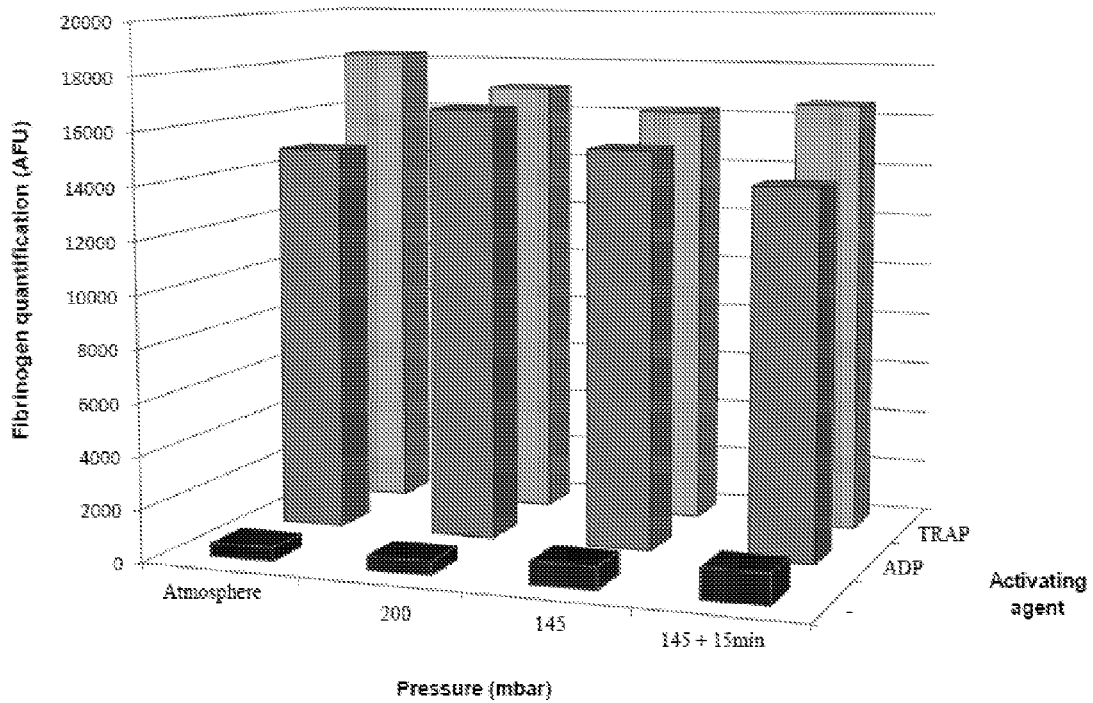
Figure 2(C)-(D)

A
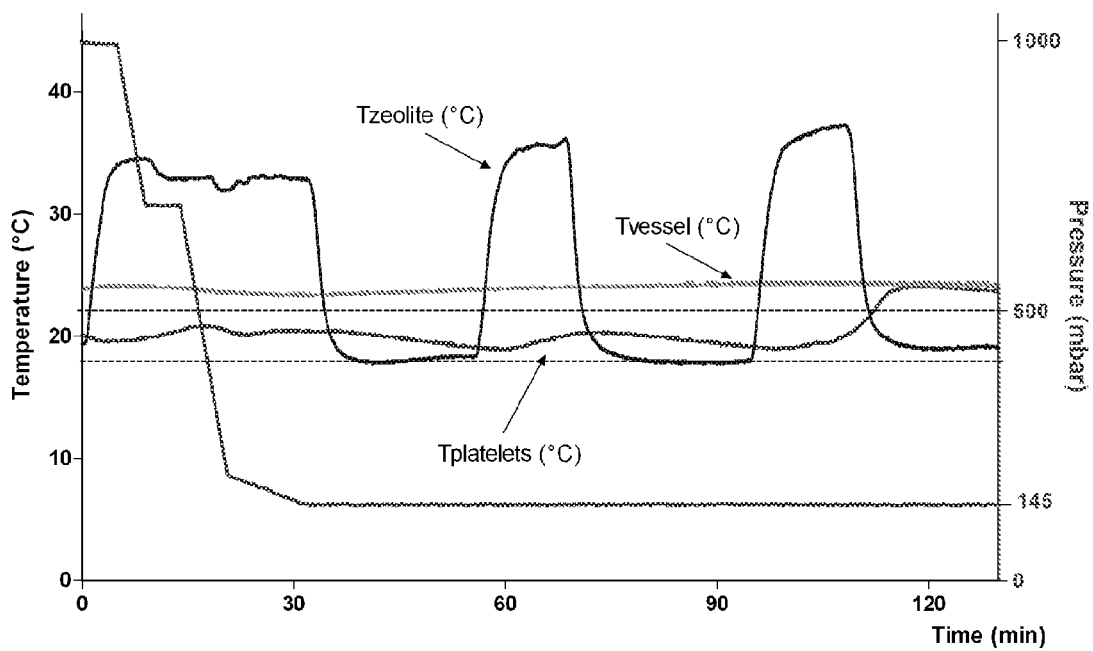
B
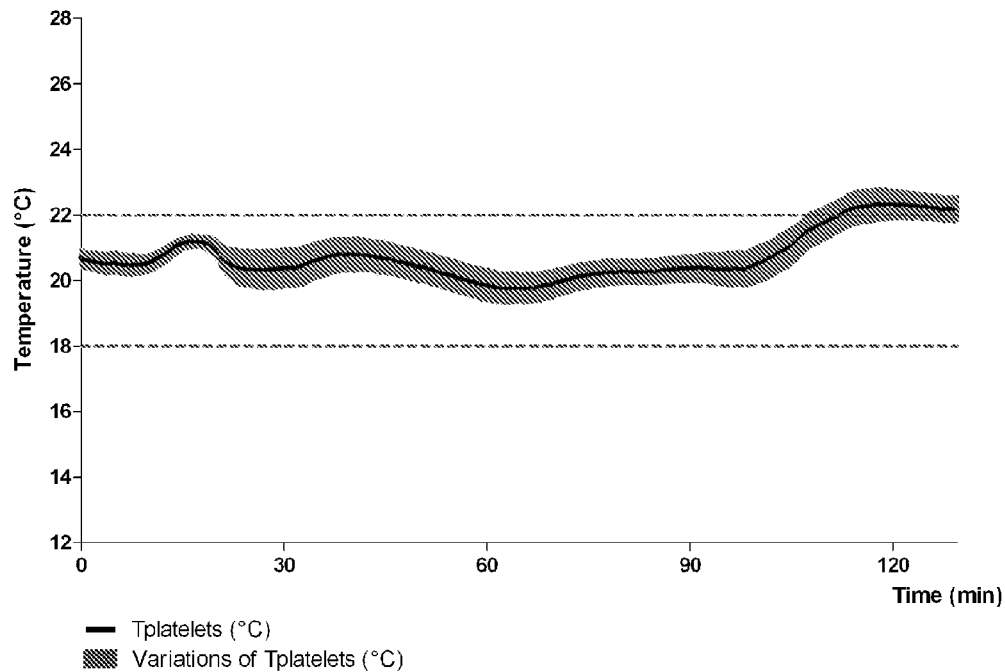
Figure 3

A
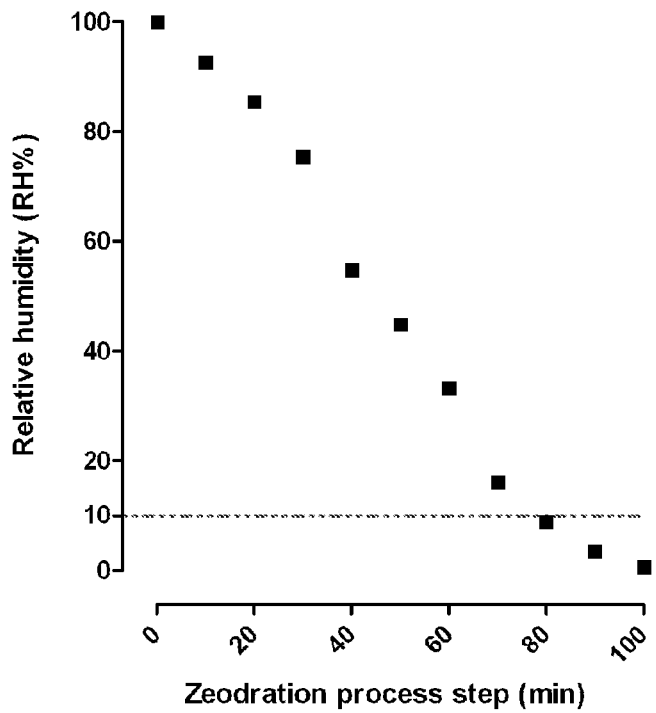
B
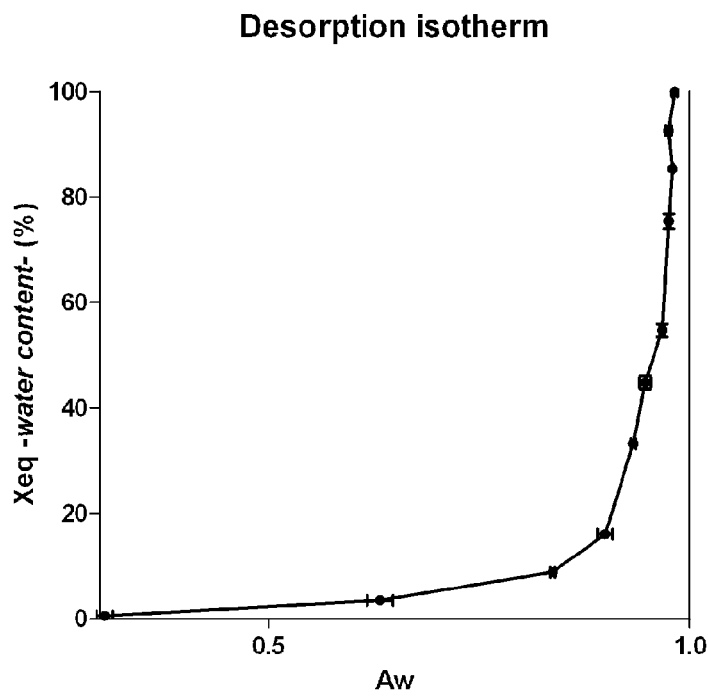
Figure 4

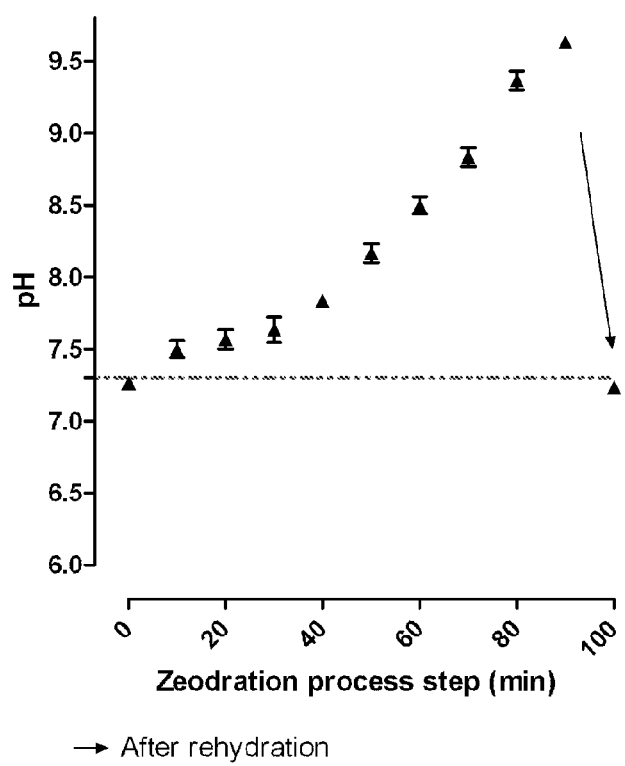
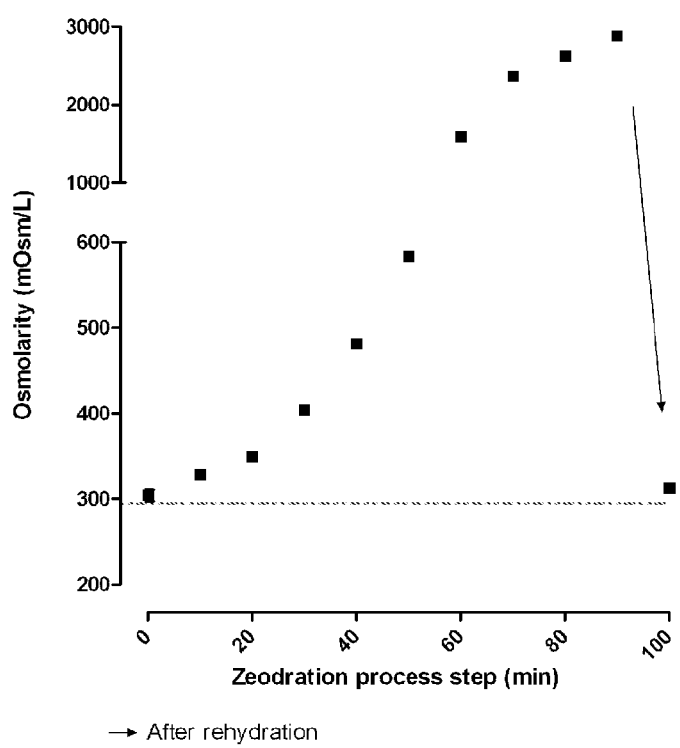
Figure 8

ZEODRATION METHOD FOR THE PRESERVATION OF BLOOD PLATELETS

RELATED APPLICATION

The present application is filed pursuant to 35 U.S.C. 371 as a U.S. National Phase application of International Patent Application No. PCT/EP2010/068320, which was filed Nov. 26, 2010, claiming the benefit of priority to European Patent Application No. EP 10 305 358.3 filed on Apr. 8, 2010. The entire text of the aforementioned applications is incorporated herein by reference in its entirety.

BACKGROUND OF THE INVENTION

Platelets are very small cellular components of the blood that comprise an outer membrane and a cytoplasm containing granules, dense bodies, dense tubular system and mitochondria. Platelets are produced in the bone marrow and survive in the circulatory system for an average of 9 to 10 days before being removed from the body by the spleen. The main function of platelets is the maintenance of hemostasis, the body's normal physiological process that prevents excessive blood loss. Hemostasis is primarily achieved by the formation of a thrombus (or blood clot) following damage to the endothelium of blood vessels.

Platelet transfusions are used extensively in the medical field, in particular for assisting in the control of bleeding and for replacing functionally defective platelets in patients. For example, platelet transfusions are administered to trauma patients who have lost significant amounts of blood, to patients undergoing chemotherapy, which is known to reduce the number of platelets and cause functional defects in remaining platelets, as well as to patients with certain platelet-depleting diseases (e.g., thrombocytopenia).

Platelets used for transfusion can come from two sources: platelet concentrates derived from units of whole blood, termed random donor platelet concentrates, or apheresis platelets obtained from a single donor by plateletpheresis, a technique which involves continuous separation of platelets from a donor, with simultaneous reinfusion of blood minus platelets back into the donor.

Whatever the mode of collection or use, platelet preservation presents problems that are not observed with the storage of whole blood or other blood components. Indeed, it has proved difficult to preserve platelets after their isolation from the body under conditions not only maintaining the biological activity of platelets but also suitable for clinical use (e.g., absence of bacterial contamination). Refrigeration of platelets is associated with several limitations. Indeed, at 4° C., platelets aggregate and undergo a morphological change after one day of storage which results in biological dysfunction. Consequently, platelets stored at 4° C. generally fail to recover functional activity and often undergo lesions with storage that cause them to be removed from the circulation following transfusion. Therefore, the standard means of storage of platelets is at room temperature (18-24° C.) with gentle agitation. However, even under these conditions, storage duration is limited to 3 to 5 days, because of a decrease in pH due to increased lactate production associated with anaerobic metabolic activity.

Since under standard storage conditions, platelets have a shelf-life of only a few days, there has been considerable interest in devising new strategies for extending storage duration and for diminishing or delaying the loss of platelet function during the storage period (Read et al., Mol. Med. Today, 1995, 1: 322-328). One of the different approaches developed makes use of cryopreservation techniques. These methods generally provide an increased number of platelets following storage. However, freezing temperatures require the addition of cryoprotectors, such as dimethyl sulfoxide, to platelets. Cryoprotectors are cytotoxic and typically leave a significant portion of the platelets with either reduced or no functional ability (Blajchman, Transf. Clin. Biol., 2001, 8: 267-271).

Other attempts to preserve platelets have included the use of platelet activation inhibitors (Bode et al., Blood Cells, 1992, 18: 361-380), of plasma-free platelet storage media (de Wildt-Eggen et al., Vax Sang, 2003, 84: 256-264), and of platelet additive solutions (Gulliksson, Transfus. Med., 2000, 10: 257-264; van der Meer, Transfus. Clin. Biol., 2007, 14: 522-525) as well as the development of platelet products (George et al., Blood, 1982, 60: 834-840; McGill et al., J. Lab. Clin. Med., 1987, 109: 127-133) and of platelet substitutes (Okamura et al., Bioconj. Chem., 2009, 20: 1958-1965; Okamura et al., Bioconj. Chem., 2005, 16: 1589-1596).

Another avenue of research for the preservation of platelets has focussed on the use of lyophilization (Aster, Proc. Natl. Acad. Sci. USA, 1995, 28: 2419-2420; Read et al., Proc. Natl. Acad. Sci. USA, 1995, 92: 397-401; Bode et al., Transf. Sci., 2000, 22: 99-105; Bode et al., Art. Cells Blood Substit. Immobil. Biotechnol., 2007, 35: 125-133). However, this technique has not yet provided satisfactory results since, even when storage is performed in the presence of protective glycoproteins, platelets preserved by freeze-drying, do not circulate in the body after transfusion.

Therefore, there is a great need for improved methods for the preservation of blood platelets suitable for transfusion. In particular, preservation methods that would allow platelets to be stored for long periods of time while maintaining their viability and bioactivity and reducing the likelihood of bacterial growth are highly desirable.

SUMMARY OF THE INVENTION

The present invention generally relates to improved methods for the preservation of blood platelets. In particular, the methods of the invention include drying the platelets by zeodration performed at about room temperature and storing the dried platelets obtained at room temperature. This operation, which is carried out under mild conditions, allows platelets to be preserved for long periods of time, i.e. several months to a year, at room temperature.

Accordingly, in one aspect, the present invention provides a method for preserving blood platelets, in particular human platelets, which comprises steps of: submitting a sample of platelets to zeodration carried out between 18° C. and 24° C. inclusive, in particular between 18° C. and 22° C. inclusive, to obtain dried platelets; and storing the dried platelets at room temperature.

In certain embodiments, submitting the sample of platelets to zeodration comprises steps of: loading the sample of platelets into a chamber (for example a chamber or vessel of a zeodrator); placing the sample of platelets contained in the chamber under vacuum; and drying the platelets under vacuum to obtain dried platelets having a relative humidity lower than or equal to 10% and a water activity lower than or equal to 0.6. In this method, the steps of placing the sample of platelets under vacuum and of drying the platelets are performed while maintaining the temperature of the platelets between 18° C. and 24° C. inclusive, in particular between 18° C. and 22° C. inclusive.

In certain particular embodiments, submitting the sample of platelets to zeodration comprises steps of: loading the sample of platelets into a chamber and let the sample of platelets stabilize for 5 minutes; decreasing the pressure of the chamber containing the platelets down to 700 mbar at a speed of 75 mbar/minutes in less than 5 minutes and let the sample of platelets stabilize at 700 mbar for 5 minutes; decreasing the pressure of the chamber containing the platelets down to 200 mbar at a speed of 75 mbar/minute in less than 7 minutes; decreasing the pressure of the chamber containing the platelets from 200 mbar down to 145 mbar at a speed of at least 5 mbar/minute; and drying the platelets at 145 mbar for between about 2 hours and about 5 hours to obtain dried platelets having a relative humidity lower than or equal to 10% and a water activity lower than or equal to 0.6. In this method, the steps of decreasing the pressure and of drying the platelets are performed while maintaining the temperature of the platelets between 18° C. and 24° C. inclusive, in particular between 18° C. and 22° C. inclusive.

In certain embodiments, in a method for preserving blood platelets according to the present invention, the sample of platelets used comprises platelets and plasma. In certain preferred embodiments, the viscosity of the sample of platelets in plasma is decreased by dilution with a synthetic medium, such as a platelet additive solution. In other embodiments, the sample of platelets used in a method for preserving blood platelets according to the present invention is obtained by isolating platelets from plasma.

In certain embodiments, zeodration is carried out in the presence of at least one platelet protective agent, i.e., an agent that provides protection against the known adverse effects of cell dehydration. The platelet protective agent may be coated on the drying support onto which the platelets are placed prior to zeodration; and/or the platelet protective agent is added to the sample of platelets prior to zeodration; and/or the platelet protective agent is incorporated into the platelets to be dried. In certain preferred embodiments, the platelet protective agent is selected from the group consisting of trehalose, maltodextrine, dextrose and any combination thereof.

In methods for preserving blood platelets according to the present invention, the step of storing the dried platelets at room temperature is performed in the absence of light and in a dry atmosphere, either under vacuum or at atmospheric pressure in the presence of an inert gas. Preservation of zeodrated platelets under these conditions can be for several months and up to one year.

In certain embodiments, a method for preserving blood platelets according the invention further comprises a step of rehydrating the dried platelets to obtain rehydrated platelets. The step of rehydrating the dried platelets may comprises steps of: submitting the dried platelets to a humidity gradient to obtain humidified platelets; and adding water to the humidified platelets to obtain rehydrated platelets. Preferably, the humidified platelets obtained have a relative humidity of at least 50%, preferably at least 65%, and more preferably between 95% and 100%, such as 98-100%. Preferably, the rehydrated platelets obtained have a relative humidity identical or substantially similar to the relative humidity of fresh platelets or platelets conserved using the conventional standard procedure.

In certain embodiments, the sample of platelets is submitted to UVA-irradiation in the presence of the psoralen, amotosalen HCl, prior to undergoing zeodration. In other embodiments, rehydrated platelets are submitted to UVA-irradiation in the presence of amotosalen HCl. This photochemical treatment inactivates any pathogens present in the platelets.

In another aspect, the present invention provides dried blood platelets that are obtained using a preservation method of the present invention. Dried platelets of the invention can be stored at room temperature, and preferably in a dry atmosphere and in the absence of light, for long periods of time of several months and up to one year. Dried platelets of the invention have a relative humidity lower than or equal to 10% and a water activity lower than or equal to 0.6.

In another aspect, the present invention provides rehydrated platelets that are obtained by rehydrating zeodrated platelets according to a rehydration method of the invention. Preferably, the rehydrated platelets of the invention have a relative humidity identical or substantially similar to the relative humidity of fresh platelets or platelets conserved using the conventional standard procedure.

In yet another aspect, the present invention provides a kit comprising dried platelets of the invention and a container containing the dried platelets. Preferably, the container is opaque and sealed to provide a dry atmosphere. This kit can be stored at room temperature for up to one year. The present invention also provides a kit comprising rehydrated platelets of the invention and a container containing the rehydrated platelets under sterile conditions.

In still another aspect, the present invention provides for the use of dried platelets or rehydrated platelets of the invention. In certain embodiments, the invention provides for the use of rehydrated platelets of the invention in transfusion. In other embodiments, the invention provides for the use of dried platelets in an assay for the diagnosis of a disorder affecting platelets such as, for example, an assay for the diagnosis of von Willebrand disease. In yet other embodiments, the invention provides for the use of rehydration platelets of the invention, or products thereof, as substitutes for animal serum in cell-based therapy and tissue engineering approaches. In still other embodiments, the invention provides for the use of rehydration platelets of the invention in drug discovery or drug development These and other objects, advantages and features of the present invention will become apparent to those of ordinary skill in the art having read the following detailed description of the preferred embodiments.

BRIEF DESCRIPTION OF THE DRAWING

FIG. 2 is a set of four graphs showing results of experiments carried out to assess platelet functionality during the step of pressure decrease. Functionality was determined by measuring the activity of GpIIbIIIa (A), of P-selectin (B), of CD63 (C) and of bound fibrinogen (D) at each step of the process in the absence of inducers (basal) and in the presence of inducers such as ADP or TRAP.

FIG. 3 is a set of two graphs showing the variations in temperature of the platelets during the zeodration procedure. (A) Variations of the temperature of the reaction vessel, of the platelets and of the zeolites and variations in pressure as a function of drying time in the presence of zeolites and under conditions where the zeodrator is placed in an air-conditioned room. (B) Reproducibility of the procedure over 9 different experiments.

FIG. 4 is a set of two graphs showing measurements of the relative humidity (HR) of platelets at different times of the zeodration process (A) and the desorption isotherm (B) illustrating that the dehydration process is progressive and homogeneous.

FIG. 8 is a set of two graphs showing the variation of pH (A) and osmolarity (B) during the zeodration process and following rehydration.

DETAILED DESCRIPTION OF CERTAIN PREFERRED EMBODIMENTS

Figure 1:
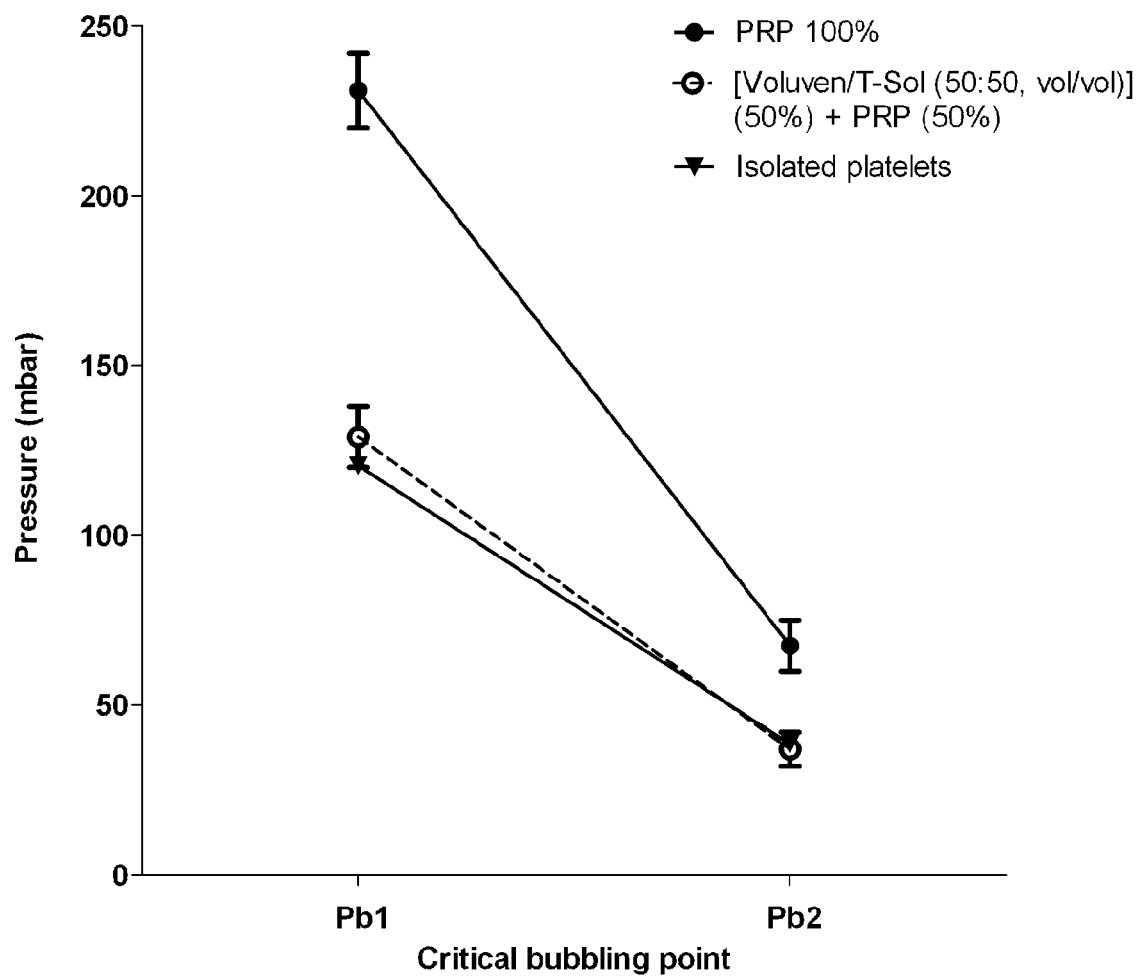
FIG. 1 is a graph showing the effect of different additive solutions (i.e., solutions in which platelets are suspended) on the critical bubbling point.

As mentioned above, the present invention provides an improved method for the preservation of blood platelets. The method involves a zeodration step performed at about room temperature (18-24° C.) and a conservation or storage step also carried out at room temperature. The treatment of blood platelets under mild conditions allows their preservation for long periods of time and maintains their viability and functionality after preservation.

I—Zeodration of Platelets

A method for the preservation of blood platelets according to the present invention comprises submitting the sample of platelets to a zeodration process performed at about room temperature to obtain dried platelets and storing or preserving the dried platelets at room temperature.

Platelets

Platelets that can be used in the methods of the present invention may originate from a human being or another mammal (e.g., primate, dog, cat, goat, horse, pig, mouse, rat, rabbit, and the like). In many embodiments of the present invention, platelets originate from a human being. In such embodiments, the platelets are termed "human platelets". In certain embodiments, platelets used in a method of the invention are obtained from a single donor. In other embodiments, platelets are obtained from several donors (e.g., two or more than two different donors of the same species). The term "donor" does not denote any particular age, and thus encompasses newborns, children, teenagers and adults.

In certain embodiments, the platelet count of a donor may be assessed. In the same or other embodiments, the blood type (ABO antigens, Rh antigens, etc) and/or human leukocyte antigens (HLA) and/or human platelet antigens (HPA) of the platelet donor is/are determined or known. This information may subsequently facilitate provision of HLA-matched and/or crossmatch-compatible platelets for transfusion. However, in other embodiments, platelets are collected without these tests being performed.

The platelets used in a method of the present invention may originate from a healthy donor (e.g., a donor known not to suffer from any particular ailment). Alternatively, the platelets may be obtained from a donor with a specific disease or disorder. For example, platelets may be obtained from a donor diagnosed with a specific disease or disorder affecting or associated with platelets, such as disorders leading to reduced platelet count (e.g., thrombocytopenia, Gaucher's disease, and aplastic anemia); alloimmune disorders (e.g., fetomaternal alloimmune thrombocytopenia); disorders leading to platelet dysfunction or reduced count (e.g., HELLP syndrome, hemolytic-uremic syndrome, chemotherapy, dengue, alpha-delta platelet storage pool deficiency); disorders featuring an elevated platelet count (e.g., thrombocytosis); disorders of platelet adhesion or aggregation (e.g., Bernard-Soulier syndrome, Glanzmann's thrombasthenia, Scott's syndrome, von Willebrand disease, Hermansky-Pudlak syndrome, and gray platelet syndrome); and disorders of platelet metabolism (e.g., induced or congenital decreased cytooxygenase activity, acquired or congenital storage pool defects).

Platelets to be preserved using a method of the invention may be obtained by any suitable method. Thus, platelets may be platelet concentrates (e.g., platelet-rich plasma) derived from units of whole blood. Whole blood can be collected by any suitable method, for example, by venipuncture into a container containing an anticoagulant such as heparin, ACD-A (anticoagulant citric acid citrate dextrose), citrate or EDTA, or from an in-dwelling arterial line into such a container. Platelet-rich plasma (PRP) can be obtained by centrifugation of whole blood, which leads to the formation of different layers: the inferior layer composed of red blood cells, an intermediate layer composed of white cells and the superior layer made up of plasma. Isolated platelets can be obtained by centrifugation of PRP, which leads to formation of a platelet pellet. The platelet pellet can then be gently agitated to resuspend the platelets in a solution. Other platelets suitable for use in a preservation method of the present invention are apheresis platelets obtained from a single donor by plateletpheresis.

In any case, platelets to be used in a method of the invention are to be obtained according to relevant national rules or recommendations.

Platelet Preparation Prior to Zeodration

If desired, prior to zeodration, the viability and/or functionality of the platelets may be tested using any suitable method. Such methods include, but are not limited to, determination of the pH of the platelet fraction; determination of lactic dehydrogenase (LDH) activity (LDH is an enzyme which is normally active inside platelets, but which is leaked outside platelets when they have undergone loss of membrane integrity); light transmission aggregometry, which measures platelet aggregation in plasma after exposure to substrates such as arachidonic acid, epinephrine, collagen or adenosine diphosphate (ADP). Other techniques for assessing platelet function include the platelet function analyzer PFA-100®, which determines high shear stress-dependent platelet aggregation in whole blood; the THROMBELASTOGRAPH® (TEG) PLATELETMAPPING™ assay, which evaluates clot strength and provides a quantitative analysis of platelet function; the VERIFYNOW™ (aspirin, $P_2Y_{12}$ and IIb/IIIa) assays, which measure platelet function based upon the ability of activated platelets to bind to fibrinogen-coated beads; and flow cytometry techniques used to assess the state of platelet activation through determination of conformation changes in membrane glycoproteins and surface expression of P-selectin and phosphotidylserine.

As reported in the Examples section below, the present inventors have found that zeodration can be carried out using platelets in plasma—their natural environment. Thus, in certain embodiments, the platelets used in a method of the present invention are present in the plasma with which the platelets were separated from whole blood or from a plateletpheresis donor. In other embodiments, the platelets used in a method of the present invention are mixed with plasma that was obtained independently from the platelets. Such plasma may be obtained from the donor who provided the platelets or alternatively, from a different donor of the same species. The zeodration may also be performed on platelets that are isolated from plasma and resuspended in a synthetic solution.

Also as reported in the Examples section below, the present inventors have found that the viscosity of the plasma sample containing the platelets should preferably be decreased by dilution prior to zeodration. In certain preferred embodiments, the viscosity of the plasma/platelets sample is decreased by dilution with a synthetic (i.e., a non-naturally occurring) medium. Synthetic media that can be used in the practice of the present invention are, in certain embodiments, preferably suitable for injection. Suitable synthetic media include, for example, platelet additive solutions that have been developed for decades as an alternative platelet suspension and storage medium (see, Ringwald et al., Transf. Med. Rev., 2006, 20: 158-164). A number of platelet additive solutions have been described, such as those disclosed in U.S. Pat. No. 6,613,566; van der Meer et al., Transf. Med., 2001, 11: 193-197; Gullikson, Transf. Med., 2000, 10: 257-264; Ringwald et al., Vox Sanguinis, 2005, 89: 11-18; Ringwald et al., Transf., 2006, 46: 236-243 and Ringwald et al., Transf. Med. Rev., 2006, 20: 158-164. Such platelet additive solutions generally comprise sodium chloride, sodium citrate and sodium acetate. Alternative platelet additive solutions include phosphate, potassium and magnesium. A number of synthetic media suitable for use in the practice of the present invention are commercially available including, but not limited to, VOLUVEN® (Fresenius Kabi), which is used in perfusion in case of hypovolemy. Similarly a number of suitable platelet additive solutions are commercially available including, but not limited to, T-SOL® (Baxter Healthcare Corporation), COMPOSOL® PS (Fresenius Kabi), PPS® and PPS+® (MacoPharma), and InterSol (Fenwal, Inc.).

The viscosity of the plasma/platelets sample is decreased in order to prevent platelet membranes from breaking due to a bubbling phenomenon that takes place when the sample is put under vacuum during zeodration. One skilled in the art will know how to select an appropriate synthetic medium (e.g., a platelet additive solution) and to determine the appropriate volume of synthetic medium (or mixture of synthetic media) to be added to the plasma/platelets sample. This can be done for example by determining the bubbling point of a series of different mixtures of synthetic medium plasma/platelets samples (see Example 1). Thus, in the practice of the present invention, any volume of synthetic medium or mixture of synthetic media may be added to the plasma/platelets sample as long as the desired result (i.e., preventing platelet membranes from breaking during zeodration due to bubbling) is attained. For example, the volume of synthetic medium may be such that the ratio of synthetic medium/plasma is about 90:10, 80:20, 70:30, 60:40, 50:50, 40:60, 30:70, 20:80, or 10:90 (vol:vol). The terms "approximately" and "about", as used herein in reference to a number, generally include numbers that fall within a range of 10% in either direction of the number (greater than or less than the number) unless otherwise stated or otherwise evident from the context (except where such number would exceed 100% of a possible value).

In the experiments presented in the Examples section below, the inventors have obtained satisfactory results using a mixture of T-SOL® and VOLUVEN® (50:50, vol:vol) added to the plasma/platelets sample in such a volume that the synthetic media/plasma ratio was 50:50 (vol:vol).

Zeodration

A preservation method according to the present invention includes submitting platelets, as described above, to zeodration carried out at about room temperature. As used herein, the term "zeodration" refers to a dehydration or drying method in which the product (which can be liquid, semi-liquid or solid) is dried under vacuum in the presence of zeolites used as water adsorbents or drying medium. As used herein, the term "zeolites" has its art understood meaning and refers to microporous, aluminosilicate minerals. Zeolites used in zeodration are in the form of particles (e.g., beads) with pores of a diameter of 4 Angstroms, which allows for the selective adsorption of water. Indeed, this diameter is slightly superior to the size of a water molecule but too small to trap any molecule bigger than water such as aromas, pigments, or other volatile molecules.

In general, during zeodration, the product to be dried is loaded into a chamber or vessel (e.g., a chamber or vessel of a zeodrator) and placed under vacuum. Under conditions of reduced pressure, the water present in the product evaporates easily and, following evaporation, is adsorbed onto the zeolites. The energy produced by the exothermic adsorption reaction is generally collected and used to heat the product during the drying cycle thereby promoting water evaporation by increasing the water vapor pressure. Zeodration may be performed in a large range of temperatures (i.e., temperatures from about −40° C. to about +60° C.). In general, zeodration is carried out at temperatures that are specifically adapted to or specifically suitable for the product to be dried. Zeodration is a mild drying process that preserves the molecular structure and organoleptic properties of the product. It is also an environmentally friendly technology because it only requires low energetic consumption; it produces little discharge (mainly water); and zeolites, used as water trap, can be regenerated over and over for long periods of time (around 3-5 years).

Drying by zeodration has been mainly applied in the food industry (in particular for the preservation of herbs, fruits, vegetables, fish, shrimps, eggs, dairy products, mushrooms, etc) as well as in the cosmetic and pharmaceutical industries (in particular for the preservation of plant extracts). Zeodration has also been proposed for drying living cells (see French patent application number FR 2 836 482 A1). However, in this case, zeodration was performed using temperatures below 0° C.

In contrast, according to the present invention, the step of drying platelets using zeodration is performed at about room temperature. In other words, the temperature of the platelets during zeodration is kept at around room temperature. As used herein, the term "at about room temperature" refers to temperatures ranging from 18° C. to 24° C. inclusive, for example from 18° C. to 22° C. inclusive.

Zeodration according to the present invention comprises a step of loading the sample of platelets into a chamber or vessel and placing the platelets under vacuum followed by a step of drying the platelets under vacuum. Placing the platelets under vacuum may be performed using any suitable protocol as long as the temperature of the platelets is kept between 18° C. and 24° C. during the whole process and as long as the protocol does not result in any significant permanent, detrimental effect on the platelets' shape, activation and functionality. One skilled in the art would know how to design and develop a protocol to attain these goals (see, for instance, Example 1 below). Similarly, the step of drying the platelets under vacuum may be carried out using any suitable protocol as long as the temperature of the platelets is kept between 18° C. and 24° C. during the whole process, the protocol used does not result in platelet structure damage, and the final relative humidity of the dried platelets is lower than or equal to 10% and a water activity lower than or equal to 0.6.

In certain preferred embodiments, placing the platelets under vacuum is carried out using a protocol comprising steps of decreasing the pressure of the chamber or vessel containing the platelets (a) from the atmospheric pressure value down to 700 mbar at a speed of 75 mbar/minutes in less than 5 minutes and let the sample of platelets stabilize at 700 mbar for 5 minutes; (b) from 700 mbar down to 200 mbar at a speed of 75 mbar/minute in less than 7 minutes; and then (c) from 200 mbar down to 145 mbar at a speed of at least 5 mbar/minute.

In such preferred embodiments, the step of drying the platelets under vacuum is carried out at a pressure of 145 mbar for a time necessary for the platelets to dry until their final relative humidity is lower than or equal to 10% and their water activity is lower than or equal to 0.6. In certain embodiments, the drying step is performed at 145 mbar for between about 2 hours and about 5 hours. These conditions have been shown to be particularly suitable for drying $3\text{-}4\times10^8$ platelets. One skilled in the art will recognize that such conditions may have to be optimized for the drying of larger quantities of platelets.

In certain embodiments, during zeodation, platelets are placed on a dish coated with polydimethylsiloxane (PDMS).

In certain embodiments, zeodration is performed in the presence of at least one protective agent. Such a protective agent may be coated on the drying support onto which the sample of platelets is placed before being submitted to zeodration. Alternatively or additionally, the protective agent may be added to the sample of platelets to be zeodrated, or yet it may be incorporated into platelets prior to zeodration. A platelet protective agent suitable for use in a preservation method of the present invention may be any suitable compound or molecule, or mixture thereof, that provides protection against the known adverse effects of cell dehydration including, but not limited to, membrane impermeabilization, protein aggregation and denaturation and fusion of intercellular compartments. A platelet protective agent is preferably biocompatible with the dehydration medium (i.e., the medium in which the platelets are submitted to zeodration). A platelet protective agent is also preferably non toxic to platelets. In embodiments where the preserved platelets are intended to be used in transfusion, the platelet protective agent is also preferably non toxic to the future recipient of the platelets. A platelet protective agent may exert its protective effects via any action mechanism. For example, a platelet protective agent may act by lowering the energy level of a platelet membrane system thereby stabilizing it during the dehydration phase. Alternatively or additionally, the platelet protective agent may act by modifying the glass transition temperature of the dehydration medium thereby allowing vitrification to take place, which ensures stability over time and therefore during the storage phase.

In certain embodiments, platelet zeodration according to the invention is performed in the presence of human serum albumin (HSA).

In certain embodiments, platelet zeodration according to the present invention is performed in the presence of a platelet protective agent selected from the group consisting of trehalose, maltodextrose, dextrose and any combination thereof. As mentioned above, such a protective agent may be coated onto the drying support and/or it may be added to the sample of platelets prior to zeodration; and/or it may be incorporated into platelets to be zeodrated. Incorporation may be carried out by any suitable method that is not detrimental to platelet structure, activation and functionality. For example, incorporation of a protective agent into platelets may be performed via the use of liposomes, since liposomes will facilitate the penetration of sugars within granule membranes.

In other embodiments, the platelet protective agent is a hydrogel containing carbohydrates that is used to sustain the platelet structure during the drying step. Particularly suitable hydrogels are the biocompatible hydrogels developed by D. Letourneur and coworkers (WO 2005/053396).

Zeodration according to the present invention may be performed using any suitable apparatus, including zeodrators that are commercially available such as those proposed by Zéodry+Plus, Millennium Energy S.A. or ZEObiofresh Vacuum Cooling Alternative, and in particular apparatuses that allow zeodration by confinement (see EP 1 740 898). Alternatively, zeodration according to the present invention may be performed using custom-made apparatuses. For example, such apparatuses may be built according to descriptions and recommendations available in the art (e.g., FR 2 836 482, FR 2 803 222; FR 2 804 750; FR 2 805 759; EP 1 740 898).

In certain embodiments, the zeodrator is let to stand at room temperature for at least one hour before each zeodration process. Alternatively or additionally, the zeodrator may be placed in an air-conditioned room, e.g., at about 20° C.

Improvements can also be brought to existing zeodrators such that they are more suitable for platelet zeodration at around room temperature. In fact, the present inventors have observed that by increasing the distance between the zeolites and the drying support containing the platelets, and by implementing the zeodrator with a thermal regulation system, it was possible to further increase the drying time while maintaining the platelets at the desired temperature range. The present inventors have also observed that placing the vacuum pump of the zeodrator outside the casing of the apparatus prevents mechanical overheating of the zeodrator, which results in a stabilization of the thermal profile of the system. Thus, in certain embodiments, a zeodrator to be used in the practice of the present invention contains at least one drying support onto which platelets are to be placed and at least one support for zeolites that are located within the same enclosure or chamber but that are far from each other. In the same or other embodiments, a zeodrator to be used in the practice of the present invention comprises a thermal regulation system. In the same or still other embodiments, a zeodrator to be used to dry platelets according to the invention comprises a vacuum pump that is located outside the casing of the apparatus.

II—Storage of Zeodrated Platelets

A method for the preservation of blood platelets according to the present invention comprises submitting the platelets to a zeodration process performed at about room temperature to obtain dried platelets and storing or preserving the dried platelets at room temperature.

Preservation or Storage of Zeodrated Platelets

Following completion of the zeodration process, the dried platelets are collected or recovered from the zeodrator (for example after breaking the vacuum of the zeodrator chamber containing the dried platelets). The dried platelets may then be preserved at room temperature (i.e., between 18° C. and 24° C.) for example in an air-conditioned room or chamber. Preferably, the platelets are stored in the absence of light and in dry atmosphere (either under vacuum, i.e., in a container sealed under vacuum, or under atmospheric pressure in the presence of an insert gas such as nitrogen and/or argon). Under these conditions, zeodrated platelets may be preserved for more than 1 week and at least up to 8 months, preferably for at least 2 weeks and up to 7 months, and more preferably for at least 1 month and up to 6 months. In certain embodiments, zeodrated platelets may be preserved at room temperature, in a dry atmosphere and in the absence of light for at least 1 year.

Preserved, Zeodrated Platelets

In another aspect, the present invention provides dried platelets that can be preserved at room temperature, wherein such dried platelets are obtained by submitting fresh blood platelets to zeodration at about room temperature, as described above. In certain embodiments, the dried platelets are contained in an opaque container sealed under vacuum. In other embodiments, the dried platelets are contained in an opaque container under atmospheric pressure in the presence of an inert gas.

Dried platelets according to the invention generally have a relative humidity lower than or equal to 10%. Indeed, an eukaryote cell is said to be dehydrated if the amount of residual water is lower than or equal to 0.1 gram per gram of dry mass (De Castro et al., Nature Biotechnology, 2000, 18: 473). In certain embodiments, the dried platelets have a relative humidity of less than 9%, less than 8%, less than 7%, less than 6%, less than 5%, or less than 4%.

Dried platelets according to the invention generally have a water activity lower than or equal to 0.6. Indeed, a product with a water activity value ≤0.6 does not present the risk of microbial growth during storage. In certain embodiments, the dried platelets have a water activity of less than 0.5, less 0.4 or less than 0.3.

As mentioned above, dried platelets according to the invention may be preserved under these conditions for more than 1 week, e.g. 2 weeks, 3 weeks or 4 weeks and up to 1 year, e.g. 9 months, 8 months, 7 months, 6 months, 5 months, 4 months, 3 months or 2 months.

III—Rehydration of Preserved, Zeodrated Platelets

According to the present invention, in certain embodiments, prior to being used, zeodrated platelets are submitted to a rehydration process. Rehydration may be performed using any suitable method, in particular any method that yields platelets with structural, viability, functionality, and bioactivity properties as close as those of fresh platelets or platelets preserved under standard conditions.

Rehydration of Zeodrated Platelets

The present invention provides a method for the rehydration of dried platelets obtained by zeodration. This method comprises two consecutive steps of (a) submitting the dried platelets to a humidity gradient to obtain humidified platelets, and (b) adding any necessary water to the humidified platelets to obtain rehydrated platelets. Preferably, the rehydration is performed at room temperature, in a sterile atmosphere, and in the absence of light. As used herein, the term "humidified platelets" refers to platelets that have a relative humidity higher than 10%, e.g., higher than 50%, preferably higher than 65% or 75%, more preferably between 95% and 100%, for example 98-100%.

Submitting dried platelets to a humidity gradient may be performed by any suitable means. For example, submitting dried platelets to a humidity gradient may include the use of a programmable humidity chamber. Such humidity chambers are commercially available, for example, from Secasi Technologies, Ineltec or Froilabo.

Following rehydration, the platelets could be conserved at room temperature (18-24° C.) with gentle agitation for up to 3 days. However, in many embodiments, the rehydrated platelets are used within a few minutes to a few hours following rehydration.

Rehydrated Platelets

In another aspect, the present invention provides rehydrated platelets that have been obtained by rehydrating dried platelets of the invention. Preferably, the rehydrated platelets are provided under a sterile atmosphere. In certain embodiments, the rehydrated platelets are contained in a flask. In other embodiments, the rehydrated platelets are contained in a bag (e.g. a biocompatible plastic bag).

Preparation of Platelets Before Use

In certain embodiments, rehydrated platelets are submitted to UVA-irradiation in the presence of the psoralen, amotosalen hydrochloride. This photochemical process, called INTERCEPT™ treatment, has been developed to inactivate a broad range of DNA- and RNA-based single and double-stranded viruses, bacteria, parasites, and leukocytes in platelet concentrates and plasma in blood bank setting (McCullough et al., Blood, 2004, 104: 1534-1541; Eastman et al., transfusion, 2005, 45: 1459-1463; Snyder et al., Transfusion, 2005, 45: 1864-1875; Pineda et al., Transfusion, 2006, 46: 562-571; Simonsen et al., Transfusion, 2006: 46: 424-433; Slichter et al., Transfusion, 2006, 46: 731-740). Amotosalen HCl prevents the replication of susceptible pathogens by blocking the replication of RNA though photochemical cross-linking. Platelets are not inactivated by the cross-linking process because they do not require nucleic acids to function, and remain therapeutically effective.

In the practice of the present invention, amotosalen HCl is added to rehydrated platelets and the mixture is exposed to UVA light (320-400 nm). Irradiation is performed for a time sufficient to inactivate pathogens present in platelets.

Alternatively, this photochemical treatment can be performed on platelets before they are submitted to zeodration. Accordingly, in certain embodiments, platelets are submitted to UVA-irradiation in the presence of amotosalen HCl prior to zeadration.

IV—Uses and Indications of Platelets Preserved via Zeodration

The methods of platelet preservation provided by the present invention render platelets more easily available and therefore more easily usable. Blood platelets preserved using a method of the present invention may have the same applications as fresh platelets or platelets conserved using the accepted standard procedure. Thus, blood platelets that have been preserved according to a method of the present invention may be used in transfusions, in methods of diagnosis, as a substitute for animal serum in cell-based therapies, as well as in research and drug development.

Platelet Transfusion

Thus, in particular, platelets of the invention may be used in transfusion. They may be administered to trauma patients who have lost significant amounts of blood, to patients undergoing chemotherapy known to reduce the number of platelets and to cause functional defects in remaining platelets, to patients undergoing bone marrow transplant, radiation treatment, organ transplant or surgeries such as cardiopulmonary bypass, as well as to patients suffering from disorders leading to reduced platelets count (e.g., thrombocytopenia, Gaucher's disease, and aplastic anemia), from alloimmune disorders (e.g., fetomaternal alloimmune thrombocytopenia), from disorders leading to platelet dysfunction or reduced count (e.g., HELLP syndrome, hemolytic-uremic syndrome, chemotherapy, dengue, alpha-delta platelet storage pool deficiency), from disorders featuring an elevated platelet count (e.g., thrombocytosis), from disorders of platelet adhesion or aggregation (e.g., Bernard-Soulier syndrome, Glanzmann's thrombasthenia, Scott's syndrome, von Willebrand disease, Hermansky-Pudlak syndrome, and gray platelet syndrome), or from disorders of platelet metabolism (e.g., induced or congenital decreased cytooxygenase activity, acquired or congenital storage pool defects).

If indicated, platelet transfusions using rehydrated platelets of the present invention should be administered according to accepted medical practice.

Methods of Diagnosis

Zeodrated platelets of the invention (i.e., in their dried form) may be used in any diagnosis method in which standardized suspensions of fixed platelets are employed. For example, zeodrated platelets of the invention may be used, in replacement of lyophilized platelets, in methods for the diagnosis of von Willebrand disease. Such methods measure the levels and/or the activity of the ristocetin cofactor. The ristocetin cofactor is a property of von Willebrand factor which promotes agglutination of platelets in the presence of the antibiotic ristocetin. Assessing the ristocetin cofactor activity allows quantitation of an activity thought to reflect von Willebrand factor activity. In such diagnosis assays, lyophilized platelets are used as standardized suspensions of fixed platelets. Zeodrated platelets of the invention may advantageously be used in these assays.

Platelets and Platelet Products as Substitutes for Animal Serum in Cell Therapy

Platelets of the invention, and/or products thereof, may be used as substitutes for animal serum in cell therapy and tissue engineering approaches. Indeed, it has been shown that platelets and platelet products (e.g., platelet lysates) can be used as a safe alternative to animal serum (e.g., fetal calf serum, fetal bovine serum, etc) for the expansion and/or differentiation of stem cells, in particular human multipotent mesenchymal stromal cells, for cell-based therapeutic strategies (Doucet et al., J. Cell. Physiol., 2005, 205: 228-236; Vogel et al., Platelets, 2006, 17: 462-469; Bernardo et al., J. Cell. Physiol., 2007, 211: 121-130; Schallmoser et al., Transfusion, 2007, 47: 1436-1446; Zaky et al., J. Tissue Eng. Regen. Med., 2008, 2: 472-481; Prins et al., Tissue Eng. Part A, 2009, 15: 3741-3751; Blande et al., Transfusion, 2009, 49: 2680-2685; Avanzini et al., Haematologica, 2009, 94: 1649-1660; Chevallier et al., Biomaterials, 2010, 31: 270-278).

Platelets for Research and Drug Development

Platelets of the invention may be used to study their biological, biochemical and/or physiological properties as well as to investigate their mechanisms of activation and to understand the regulation of platelet function. Similarly, platelets that are obtained from patients with disorders associated with platelet dysfunction and that are preserved according to the present invention may be useful in the study of abnormal or defective platelets.

The development of effective anti-platelet agents has been hampered, at least partially, by a lack of available platelets. Yet, no other single cell type is responsible for as much morbidity and mortality as the platelet and, as a consequence, it represents a major target for therapeutic intervention. Indeed, the need for novel anti-platelet agents is all the more important that the clinical burden of cardiovascular diseases is set to increase with an ageing population and increasing levels of obesity.

Platelets of the invention, which are more easily available than fresh platelets, or platelets preserved using the conventional standard procedure, may be useful in the development of novel therapeutics.

V—Kits

In another aspect, kits are provided that comprise blood platelets of the invention. More specifically, the invention provides kits that can be used in different settings (e.g., in hospitals or on location at accident sites or war sites, in diagnostics or experimental laboratories, or in research facilities) and for different applications (e.g., transfusions, diagnosis, cell therapy, tissue engineering, research and drug development).

Thus, in certain embodiments, a kit comprises zeodrated (i.e., dried) platelets according to the invention and a container containing the zeodrated platelets. Preferably, the container is opaque and either sealed under vacuum or under atmospheric pressure in the presence of an inert gas. In other embodiments, a kit comprises rehydrated platelets according to the invention and a container containing the rehydrated platelets. Preferably, the container preserves the rehydrated platelets under sterile conditions. Such a kit may be stored at room temperature for up to one year.

A kit of the invention may further comprise instructions for preserving the zeodrated platelets, and/or instructions for rehydrating the zeodrated platelets, and/or instructions for using the rehydrated platelets. Depending on the intended use, a kit may further comprise one or more of: suspension buffer and/or reagents, rehydration buffer and/or reagents, injection buffer and/or reagents, platelet additive solution and/or reagents, plasma, physiological solution and/or reagents, amotosalen HCl, rehydration means, UVA-irradiation means, and injection means.

The different additional reagents included in an inventive kit may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers (e.g., vial, ampoule, test tube, flask, bottle or assay plate) suitable for conducting certain procedures (e.g., suspension, rehydration, testing) may also be provided. The individual containers of the kit are preferably maintained in close confinement for commercial sale.

A kit may also contain a notice in the form prescribed by a governmental agency regulating the manufacture, use or sale of pharmaceuticals or biological products.

EXAMPLES

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

The goal of the present study was to develop a drying process by zeodration carried out under positive temperatures, which can be applied to blood platelets. The first step of the study (Example 1) was performed using a basic zeodrator (Zeodry+Plus, ref.: 3351), while the rest of the study (Example 2) was carried out using a more sophisticated high-performance zeodrator (Zeodry+Plus, ref.: 3354), which allowed numeric recording of the data.

Example 1

Optimization of Zeodration Protocol

1. Preliminary Experiments

Preliminary experiments were carried out using platelets (platelet concentrates and apheresis platelets) obtained in transfusion centers. Such experiments have shown that (1) zeodrating platelets should preferably be carried out using platelets in plasma and (2) the viscosity of the plasma/platelets sample should preferably be decreased by dilutions with a suitable synthetic medium.

The present inventors have investigated several dilutions of plasma and synthetic media such as INTERSOL®, T-SOL®, VOLUVEN® and mixtures with different proportions of these synthetic media. The results obtained (FIG. 1) led the inventors to select a mixture of T-SOL® and VOLUVEN® in a 50:50, vol:vol ratio to dilute a plasma/platelets sample in a 50:50, vol:vol ratio.

Under these conditions of dilution, the morphology of platelets that are dried in a conventional heating chamber between 18° C. and 22° C. in the absence of zeolites does not undergo significant changes.

2. Summary of Preliminary Results Obtained in Zeodration Experiments

The results obtained during the first step of the study have allowed the inventors to determine the effects of pressure decrease and temperature decrease on blood platelets as well as to establish an optimized protocol for zeodration. This optimized protocol comprises: a first step in which the pressure ($P_{atm}$) is decreased at a speed of $dP/dt_1$=200 mbar/minute down to 200 mbar in less than 5 minutes, a second step in which the pressure is decreased at a minimal speed of $dP/dt_2$=5 mbar/minute down to 145 mbar, and then a third step in which the pressure is maintained at 145 mbar during the drying of platelets. Use of these conditions was found to allow the temperature of the blood platelets to be maintained in the desired range of 18-22° C.

This protocol was established (and validated) by measuring the activation state of the platelets at each step of the process. In addition, the inventors have assessed platelet functionality at the end of the protocol, in the presence of physiological inducing agents, such as adenosine diphosphate (ADP), collagen, and the peptidic agonist of thrombin receptor (TRAP—thrombin receptor-activating peptide). This functionality was measured using two different approaches: (1) use of flow cytometry to analyze markers of platelet activation, which provided information about the ability of platelets to expose a functional receptor of aggregation and to release granules; and (2) use of an aggregometer to measure platelet aggregation, which provided information about the platelets' aggregation capacity itself.

In the flow cytometry experiments, a sample of starting platelets and a sample of liquid fraction obtained at the end of the protocol were each incubated with antibodies specific of markers of platelet activation (CD62P, activated GpIIbIIIa, CD63, and fibrinogen) and with activation inducers (adenosine diphosphate—ADP used at a concentration of 8 µM; and thrombin receptor activating peptide—TRAP used at a concentration of 5 µg/mL). Following a 30 minute incubation at room temperature and in the absence of light, and after a ⅕₀ dilution (PBS 1×), the suspension was analyzed by flow cytometry.

The results obtained are presented on FIG. 2. They show that platelet functionality is maintained all along the pressure decrease protocol and that at low pressure (≥145 mbar), the platelets remain capable of undergoing degranulation (expression of P-selectin) and aggregation (expression of activated GpIIbIIIa) in the presence of ADP or of TRAP. A decrease in functionality that would take place later in time would therefore be linked to a dehydration effect.

Aggregation measurements were carried out using an aggregometer (Chronolog equipped with the software Aggrolink—Kordia) to determine the variations in optical transmission in platelets samples. The optical density of a platelet suspension or of a plasma rich in platelets (PRP) decreases with increasing platelet aggregation: the medium becomes clearer and the optical transmission increases. The reference used for the PRP was a plasma poor in platelets (PPP). The reference used for the platelets obtained at the end of the pressure decrease protocol was PPP diluted 1:1 in T-Sol/Voluven that was submitted to the same pressure decrease protocol. The inducers used (ADP at 5, 2.5, 1.25 and 0.625 µM and collagen at 0.8 and 1.2 µM) were diluted in physiological solution and injected in the aggregometer cuvettes at t=0 using a Hamilton syringe. The content of the measure container was agitated (1100 rpm) and maintained at a temperature of 37° C. However, the results obtained so far were inconclusive, due to the fact that the platelet suspensions tested were too concentrated to allow the aggregometer to provide reliable measurements. Additional experiments are in progress.

Example 2

Determination of Drying Time

The drying time (i.e., the duration of the drying step) is an important parameter since it provides information regarding: (i) the performance of the process, (ii) the level of stress that is applied to the blood platelets, and (iii) the feasibility of up-scaling the process towards a pre-industrial step. The drying time must be as short as possible while allowing the platelets to be efficiently preserved and the temperature process to be maintained between 18 and 22° C.

First, the inventors have analyzed the thermal profiles of the platelets, the zeolites and the chamber. They then measured the relative humidity of platelets in order to determine the drying time to be used. Finally, the water activity of platelets was measured in order to assess the long-term conservation of zeodrated platelets.

For each assay, the conditions of pressure and of temperature were recorded using the zeodrator. The nature and amounts of the products (PRP diluted in T-Sol/Voluven) were identical to those used in Example 1.

1. Pressure Decrease and Dehydration in the Presence of Zeolites

When the dehydration step was performed in the absence of zeolites, the present inventors were able to stably maintain the blood platelets in a temperature range of 18-22° C. for time periods shorter than 2 hours. The goal was then to find conditions allowing a drying step to be performed in the presence of zeolites and the platelet temperature to be stably maintained between 18-22° C. for several hours. However, water adsorption by zeolites is an exothermal reaction which can be expected to result in a modification of the temperature of the reaction vessel. Indeed, the inventors observed an increase of the platelets temperature beyond 22° C. about two hours (132 minutes) after the beginning of the drying step.

Several steps were undertaken to solve this problem. In order to prevent the mechanical overheating of the zeodrator from disrupting the thermal profile of the system, the zeodrator's pump was placed outside the casing. Furthermore, the zeodrator was let to stand at room temperature for at least 1 hour before each test. In addition, since the thermal equilibrium of the working zeodrator was observed to be highly dependent on the ambient temperature, the zeodrator was placed in an air-conditioned room.

The results obtained using these conditions are presented on FIG. 3. They show that the platelets temperature can be stably maintained between 18° C. and 22° C.

In order to further decrease the drying time during which the platelets temperature have to be maintained in the desired range, the present inventors have submitted several suggestions to a zeodrator manufacturer: increasing the distance between the zeolites and the reaction vessel or drying support containing the product to be dried (platelets), and implementing the zeodrator with a thermal regulation system (both heating and cooling regulation). The results obtained have shown that, when the modified zeodrator is used in an air-conditioned room at 20° C., the platelets temperature can be maintained between 18° C. and 22° C. for the required time which, depending on the initial amount of platelets submitted to zeodration, may vary from about 2 hours to about 5 hours.

2. Relative Humidity and Dehydration Speed Evolution

In order for the platelets to be totally inactivated by the drying, the final relative humidity must be lower than 10% (De Castro et al., Nature Biotechnology, 2000, 18: 473).

Before the dehydration step, the drying support was placed in a dry chamber at 90° C. for 30 minutes to eliminate any water adsorbed on the polystyrene. The drying support was then manipulated using pliers and maintained in a dry atmosphere (dessicator). Right before the experiment, the drying support was let to stand at room temperature for 30 minutes. To the drying support, 2 mL of the solution of PRP diluted in T-Sol/Voluven were added and the drying support containing the PRP sample was weighted ($m_i$). PRP samples were placed in the vessel and submitted to zeodration for different times. Then, the samples were weighted again ($m_z$) and placed in a dry chamber at 110° C. for 24 hours. Finally, the weight of the dried final mass ($m_f$) was measured. The percentage of relative humidity is calculated using the following formula:

$$HR\% = 100 - \left[\frac{(m_i - m_z)}{(m_i - m_f)} \times 100\right]$$

The percentage of relative humidity of the platelets was measured at each step. The results obtained are presented on FIG. 4A. From these results, it is possible to estimate the drying time (i.e., the time necessary to obtain a final relative humidity lower than 10%) to be between about 2 hours and about 5 hours depending on the number of platelets submitted to zeodration and on the size of the chamber. FIG. 4B illustrates the desorption isotherm (one of the characteristics of the process). The curves does not show any brutal change over time, indicating that water is eliminated progressively.

Figure 5:
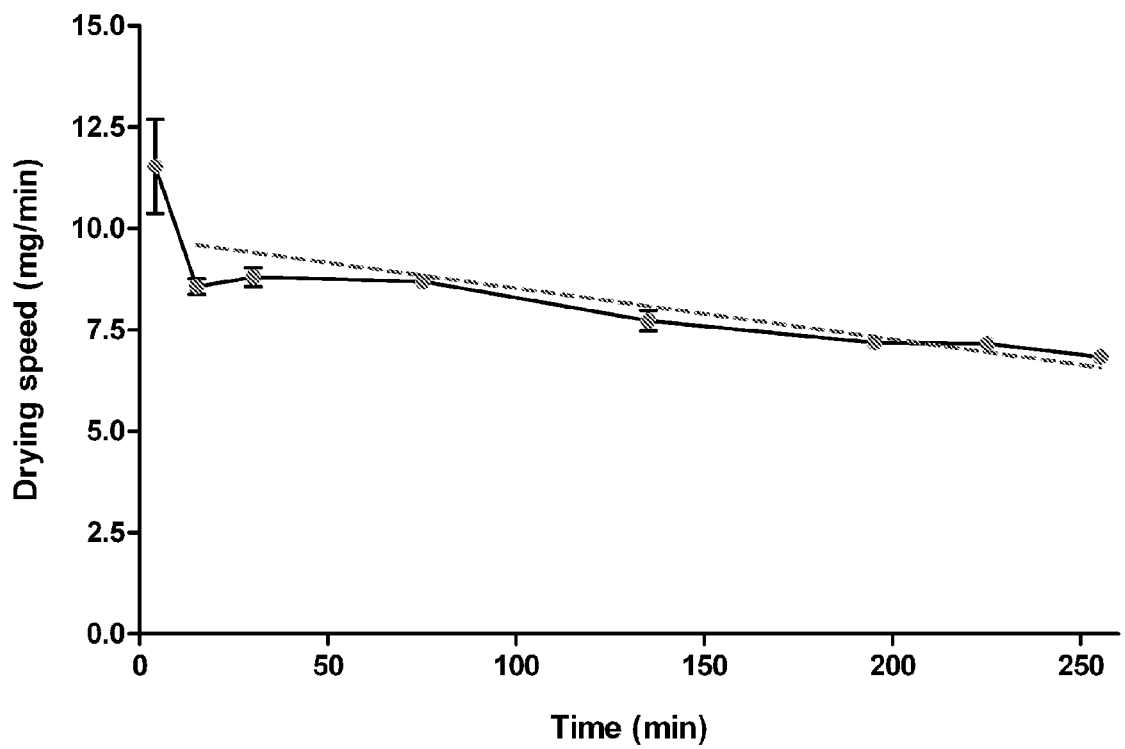
FIG. 5 is a graph showing the variations in the dehydration speed as a function of time during the zeodration process.

It is also possible to calculate the dehydration speed, expressed in milligrams of water eliminated by minute (FIG. 5). Due to the large amount of free water available, the dehydration speed is maximal at the beginning of the pressure decrease step. From 200 mbar, the dehydration speed decreases in a quasi linear fashion: the dehydration conditions are mild and without any drastic water loss that could destroy platelet membranes.

3. Drying Validation: Measure of Activity Water

Water activity (Aw) measurement is an analysis complementary to relative humidity measurement, which was performed to confirm the satisfactory preservation of platelets. Aw values were obtained using a water activity-meter (Novasina), which determines the water activity of a sample in relation to the water activity of pure water by measuring the equilibrium relative humidity with a hygroscopic probe. Equilibrium relative humidity (ERH), expressed as a percentage, is directly related to water activity:

$$Aw = ERH/100$$

A product with an Aw value ≤0.6 does not present the risk of microbial (bacterial, yeast, mold) growth.

Figure 6:
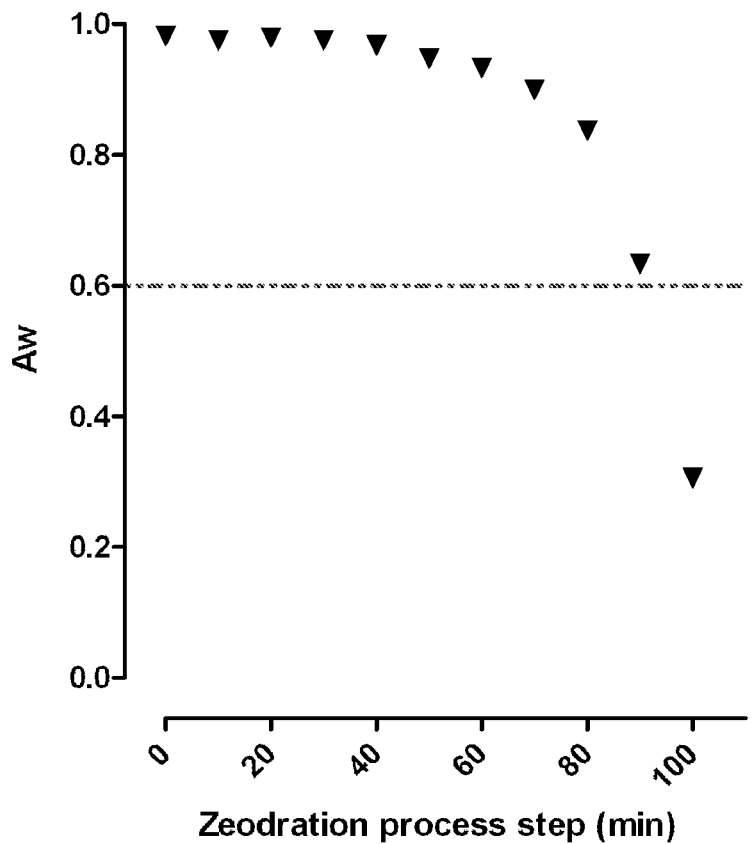
FIG. 6 is a graph showing the variations in the water activity as a function of time during the zeodration process.

The amount of product necessary to perform a Aw measurement being about 1 gram, dried platelets obtained in 10 different, successive preparations (drying time of 240 minutes) were pooled together. The Aw measurement, which was performed at 25° C. for 10 minutes, led to an Aw value of 0.302 (FIG. 6). This result suggests that dried platelets prepared using a zeodration method according to the invention can be stored with no risks of microbial development.

The dry mass was also determined using a halogen moisture analyzer (thermobalance) to confirm the results obtained. The dry mass was determined to be 94.99%, corresponding to a relative humidity of 5.1%, which is in agreement with the values determined by the method described above. Dehydrated platelets stored for 10 days did not accumulate humidity over time. This further confirms that long-term preservation of zeodrated platelets according to the invention is feasible.

4. Conclusions

Even at this stage of the development of a process for the preservation of blood platelets, the advantages of zeodration are obvious. Zeodration can be applied to platelets since the process can be carried out at temperatures at which platelets are preserved. Moreover, a drying time of only 4 hours is necessary while lyophilization (of the same quantity of product) would require several dozens of hours. In addition, because of the conditions of temperature and pressure used in the zeodration process according to the present invention, the level of stress applied to the platelets is also much more limited than that applied through lyophilization.

In order to preserve zeodrated platelets under the best conditions, storage of zeodrated platelets is preferably performed in the absence of light and under vacuum.

Example 3

Solutions to the Drying Generated Problems

As of now, a problem of heterogeneous drying, associated with surface tension, has been identified and remains to be solved.

This could be overcome by using an agent to coat the drying support (for example albumin or PDMS (FIG. 7) may be used to coat the drying support onto which the platelets are to be placed to be zeodrated), and/or by using a trehalose-type drying support, and/or by adding surface active agents (surfactants) that are biocompatible with the dehydration medium. Solving the problems linked to drying is the goal of the third step of the present study.

1. Anhydrobiotic Engineering

Anhydrobiotic engineering, a new research avenue in life science which emerged at the beginning of the 2000s, aims at studying and optimizing the resistance of biological products to dehydration. Generally, the goal is to improve cell tolerance to osmotic shocks, to temperature and pressure variations, and to radiations (Huang et al., Method in Enzymology, 2007, 428: 269-277). In the instant case of blood platelets, the protection to radiations will be obtained by using a container (for the platelets) that is opaque and sealed under vacuum. However, pressure, temperature and osmotic stress generate irreversible damages that can affect platelet activation.

Thus, as known in the art (Wolkers et al., Comp. Biochem. Physiol., 2001, 131:

535-543; Clegg et al., Comp. Biochem. Physiol., 2001, 128: 613-624), the main problems that will have to be resolved are associated with:

membrane impermeabilization and membrane fixation: due to a decrease in water content as a function of time (during the drying process), membrane phospholipids undergo strong intermolecular interactions to stabilize the bilayer. Membrane fluidity, which is required for platelet activity, is therefore lost or at least extensively reduced.

protein aggregation and denaturation: for the same reason, the entropy of the system increases with lack of water and proteins exhibit a tendency to undergo destructuration and aggregation because less and less hydrogen bonds are present. Enzymatic and signaling activities of platelets are consequently strongly reduced.

fusion of intercellular compartments: this factor results from osmolarity variations and from structural modifications of proteins and lipids mentioned above. However, platelet compartmentation plays a crucial role in the dynamic of activation and recruitment of neighboring platelets.

Several agents are known that decrease these adverse effects during dehydration. A supplemental constraint exists in the case of platelets that are intended for transfusion: such an agent must be suitable for transfusion to a patient.

2. Selecting Platelet Protective Agents

Amongst known anhydro-protector agents, carbohydrates are particularly well suited to the needs of the present study. Indeed, as known in the art (Crowe et al., Ann. Rev. in Physiol., 1998, 60: 73-103; Tunnacliffe et al., Cryobiology, 2001, 43: 124-132), sugars are capable of stabilizing cells during the phases of dehydration and of storage according to two principles:

water replacement hypothesis (WRH): the high number of hydrogen interactions available allows stabilization of macromolecules and membranes. When molecular water is removed, it is necessary to add alcohol groups capable of very quickly and specifically lodging itself in the holes that have become vacant. Sugars provide such alcohol groups; they lower the energy level of the membrane system and stabilize it during the dehydration phase.

vitrification hypothesis (WRH): all the hydrogen bonds form a large scale network allowing vitrification (glass transition) of the medium. This vitrified state ensures the stability over time and therefore during the storage phase.

However, the sugars are not all suitable for an application in anhydrobiosis. Two characteristics are crucial: (1) the glass transition temperature ($T_g$) of the sugar; and (2) its molecular weight ($M_w$) since there is a strong correlation between the molecular weight and the cytotoxicity/protective ability. Indeed, as known in the art (Puhlev et al., Cryobiology, 2001, 42: 207-217), the cytotoxicity of a sugar increases as its $M_w$ increases while the protective ability of a sugar decreases as its $M_w$ increases.

3. Advantages of Trehalose Different sugars could be suitable including, for example trehalose, maltodextrose and dextrose. Amongst the sugar candidates fulfilling the requirements mentioned above, trehalose is one of the most promising. Trehalose is the subject of a large number of scientific articles dealing with anhydrobiosis and cryobiology (Eroglu et al., Nature Biotechnology, 2000, 18: 163-167). Trehalose is a disaccharide ($\alpha,\alpha$-1,1 linked glucose dimer—see FIG. 8A), which exhibits the following advantages:

it is easily soluble (68.9 g/100 g water at 20° C.), its $T_g$ is high (110° C., while glucose's $T_g$ is 31° C. and saccharose's $T_g$ is 65° C.), its molecular weight is low et it is present in numerous organisms (this has resulted in a series of biocompatibility studies that proved to be positive—trehalose is a non-reducing sugar, therefore it will not react with amino acids or proteins during the dehydration and storage phases), it is stable at low pH, even at high temperature (in contrast to other disaccharides, trehalose does not undergo hydrolysis and therefore will not be participating in oxidation reactions—Maillard reactions—with amino acids or proteins present in the product), it is able to reduce surface tensions in the product (due to its high wettability, it should therefore provide a satisfying, homogeneous dehydration, and facilitate rehydration—see FIG. 8B—Lebret et al., J. Phys. Chem. B, 2005, 109: 11046-11057).

However, trehalose exhibits a considerable disadvantage: due to its steric hindrance, it does not easily cross membranes. It can be internalized via endocytosis but only in limited quantities. Glucose transporters are unable to perform trehalose transport. But, in order to ensure maximum protection, the outer surface and interior volume of the cell must be loaded with trehalose.

A priori, there are at least four internalization techniques applicable in vitro:

thermic shock—this process is suitable for cells that are not very thermosensitive, but is not applicable to platelets, electroporation and ultrasound—processes that are known to result in an important alteration of cell structure (S Zhang et al., Cryobiology, 2009, 59:135-140), controlled porosity—process in which a perforating agent (streptolysine) is added which creates temporary membrane pores. However, this technique is not applicable in the case of platelets intended for transfusion, and liposomes—this seems to be the most suitable option for the case under study (C. Keil et al., Thromb. Haemost., 2005, 94: 404-411). The goal is to synthesize very small liposomes, containing phospholipids analogous to platelets' phospholipids, and to highly load these liposomes with trehalose in order not to modify the platelet mean volume.

4. Other Drying Generated Problems

Figure 7:
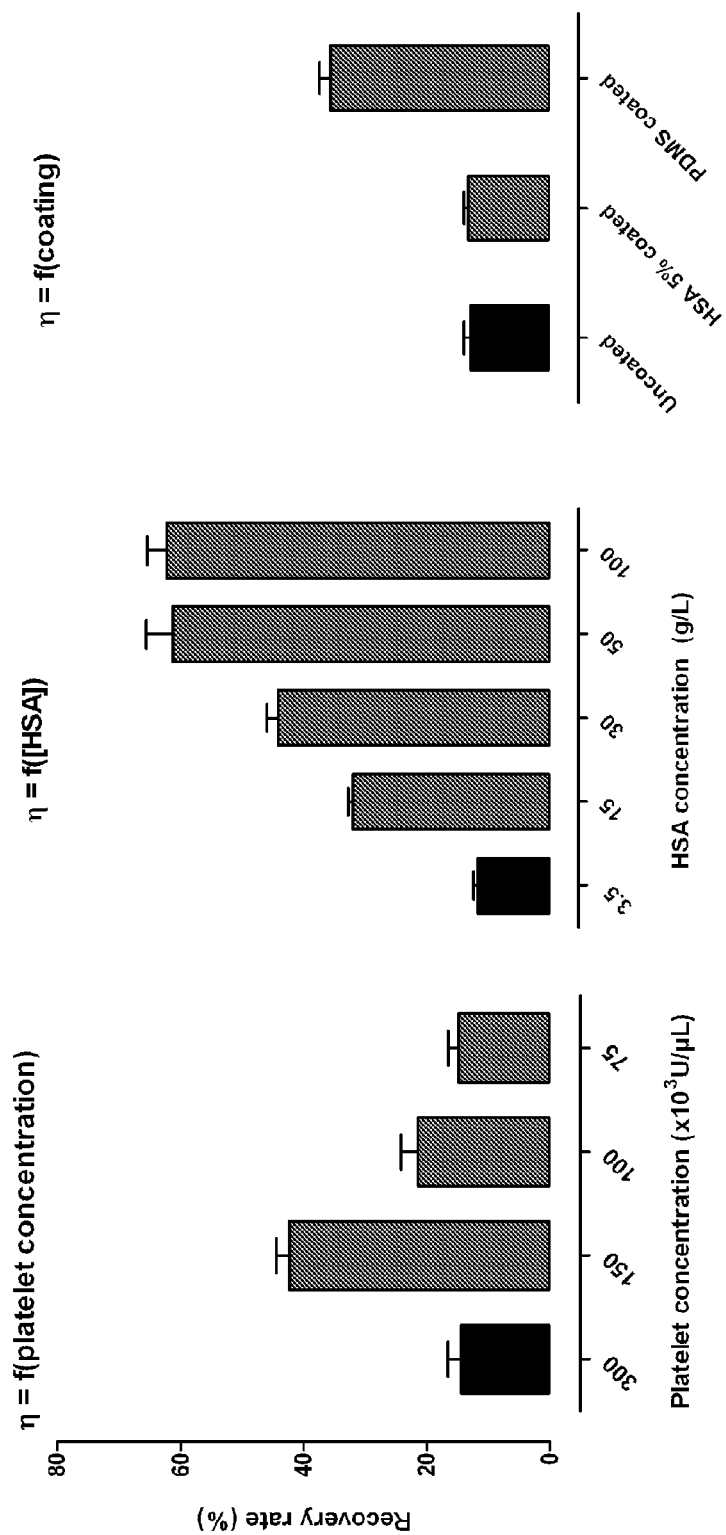
FIG. 7 is a set of three graphs showing the yield of platelet recovered after zeodration as a function of platelet concentration (left), concentration of HAS added to the platelet suspension (center), and when the zeodration is carried out with platelets placed on a dish coated with either HAS or PDMS (right).

As shown by FIG. 7, the platelet concentration may also be a factor that needs to be controlled to optimize the zeodration process.

FIG. 8 shows that the pH (FIG. 8A) and the osmolarity (FIG. 8B) of the sample of platelets increase during the zeodration process. The increase in pH could be avoided by lowering the pH of the initial sample of platelets placed in the chamber (for example to pH 6 instead of pH 7.4). The osmolarity problem could be solved by (1) adding HSA to the platelet suspension—replacing salts with highly charged ions will help decrease the initial osmolarity, and/or (2) using chelating agents to minimize the increase in osmolarity.

Thus, in certain embodiments of the present invention, the pH of the sample of platelets placed in the zeodration chamber is lowered. In other embodiments, the osmolarity of the sample of platelets placed in the zeodration chamber is lowered. In yet other embodiments, both the pH and the osmolarity of the sample of platelets placed in the zeodration chamber are lowered.

OTHER EMBODIMENTS

Other embodiments of the invention will be apparent to those skilled in the art from a consideration of the specification or practice of the invention disclosed herein. It is intended that the specification and examples be considered as exemplary only, with the true scope of the invention being indicated by the following claims.

The invention claimed is:

1. A method for preserving blood platelets comprising steps of:

submitting a sample of platelets to zeodration carried out between 18° C. and 24° C. inclusive to obtain dried platelets, and storing the dried platelets at room temperature, wherein zeodration comprises steps of:

loading the sample of platelets into a chamber;

decreasing the pressure of the chamber containing the platelets down to 700 mbar at a speed of 75 mbar/minute in less than 5 minutes;

allowing the sample of platelets to stabilize at 700 mbar for 5 minutes;

decreasing the pressure of the chamber containing the platelets from 700 mbar down to 200 mbar at a speed of 75 mbar/minute in less than 7 minutes;

decreasing the pressure of the chamber containing the platelets from 200 mbar down to 145 mbar at a speed of at least 5 mbar/minute; and drying the platelets at 145 mbar for between about 2 hours and about 5 hours to obtain dried platelets having a relative humidity lower than or equal to 10% and a water activity lower than or equal to 0.6, wherein the steps of decreasing the pressure and of drying the platelets are performed while maintaining the temperature of the platelets between 18° C. and 24° C. inclusive.

2. The method for preserving blood platelets according to claim 1, wherein the sample of platelets contains platelets, plasma and platelet additive solution such that the viscosity of the sample of platelets is lower than the viscosity of a sample of platelet-rich plasma, of apheresis platelets, or of washed platelets.

3. The method for preserving blood platelets according to claim 1, wherein zeodration is carried out in the presence of at least one platelet protective agent.

4. The method for preserving blood platelets according to claim 3, wherein the platelet protective agent is a hydrogel containing carbohydrates.

5. The method for preserving blood platelets according to claim 1, wherein storing the dried platelets at room temperature is performed for more than 1 week and up to at least 9 months.

6. The method for preserving blood platelets according to claim 5, wherein storing the dried platelets at room temperature comprises storing the dried platelets in the absence of light and in a dry atmosphere.

7. The method for preserving blood platelets according to claim 1, further comprising a step of rehydrating the dried platelets to obtain rehydrated platelets.

8. The method for preserving blood platelets according to claim 7, wherein the step of rehydrating the dried platelets comprises steps of:

submitting the dried platelets to a humidity gradient to obtain humidified platelets with a relative humidity of at least 50%; and adding water to the humidified platelets to obtain rehydrated platelets.

9. The method of preserving blood platelets according to claim 1, further comprising a step of:

submitting the sample of platelets to UVA-irradiation in the presence of amotosalen HCl prior to zeodration to inactivate any pathogen present in the sample of platelets; or rehydrating the dried platelets to obtain rehydrated platelets and submitting the rehydrated platelets to UVA-irradiation in the presence of amotosalen HCl to inactivate any pathogen present in the rehydrated platelets.

10. The method according to claim 1, wherein the blood platelets are human blood platelets.

11. The method according to claim 3, wherein the platelet protective agent is selected from the group consisting of trehalose, maltodextrine, dextrose, HSA, PDMS, and any combination thereof.

12. The method according to claim 8, wherein the relative humidity is of at least 65%.

13. The method according to claim 8, wherein the relative humidity is between 95% and 100%.

14. A method for preserving blood platelets comprising steps of:

submitting a sample of platelets to zeodration carried out between 18° C. and 24° C. inclusive to obtain dried platelets; and storing the dried platelets at room temperature; and rehydrating the dried platelets to obtain rehydrated platelets, wherein the rehydrating step comprises:

submitting the dried platelets to a humidity gradient to obtain humidified platelets with a relative humidity of at least 65%; and adding water to the humidified platelets to obtain rehydrated platelets.

15. The method according to claim 14, wherein the relative humidity is between 95% and 100%.

* * * * *